United States Patent [19]

Rice et al.

[11] Patent Number: 4,668,647
[45] Date of Patent: May 26, 1987

[54] IRON CARBIDE-BASED CATALYST PRODUCED IN THE PRESENCE OF LASER RADIATION

[75] Inventors: Gary W. Rice, Station; Rocco A. Fiato, Scotch Plains; Stuart L. Soled, Pittstown, all of N.J.

[73] Assignee: Exxon Research and Engineering Company, Florham Park, N.J.

[21] Appl. No.: 735,769

[22] Filed: May 20, 1985

[51] Int. Cl.$^4$ .................. B01J 37/34; B01J 27/22
[52] U.S. Cl. .................. 502/5; 204/157.41; 423/439; 502/177; 502/183; 502/184; 502/185; 518/717; 518/719; 518/721
[58] Field of Search .................. 502/5, 522, 177–179, 502/183–185; 423/439; 204/157.1 R, 157.1 H, 157.41; 427/53.1

[56] References Cited

U.S. PATENT DOCUMENTS

| | | | |
|---|---|---|---|
| 2,535,042 | 12/1950 | Cohn et al. | 502/177 |
| 2,608,535 | 8/1952 | Gillespie | 502/177 |
| 3,494,738 | 2/1970 | Gray et al. | 423/439 |
| 3,885,023 | 5/1975 | Gray et al. | 423/439 |
| 4,468,474 | 8/1984 | Gupta et al. | 502/5 |

FOREIGN PATENT DOCUMENTS 731295 2/1943 Fed. Rep. of Germany .

OTHER PUBLICATIONS

Brennstoff-Chem. 7, 97 (1926).
Hall et al., J. Soc. Chem. Ind. London 65, 128 (1946).
Weller, J. Am. Chem. Soc. 69, 2432 (1947).
Kummer et al., J. Am. Chem. Soc. 70, 3632 (1948).
Malan et al., Brennstoff-Chem, 42, 209–212 (1961).
SPIE 458, Appl. of Lasers to Industrial Chemistry, 131–139 (1984).
Catal. Rev.-Sci. Engr. 21, 1980 p. 225 (Kolbol, Rulek).
Gilbert, A. G., Sulzman, K.G.P. *J. Electrochem. Soc.*, 1974, 121, 832–834.

Primary Examiner—P. E. Konopka
Attorney, Agent, or Firm—E. Thomas Wheelock

[57] ABSTRACT

This invention relates to a finely divided iron carbide-based catalyst which is produced by a gas phase pyrolytic decomposition reaction driven by a laser. The catalysts may be used to produce various hydrocarbons, including olefins, from CO and $H_2$.

16 Claims, 1 Drawing Figure

Figure 1. Laser Synthesis Reactor

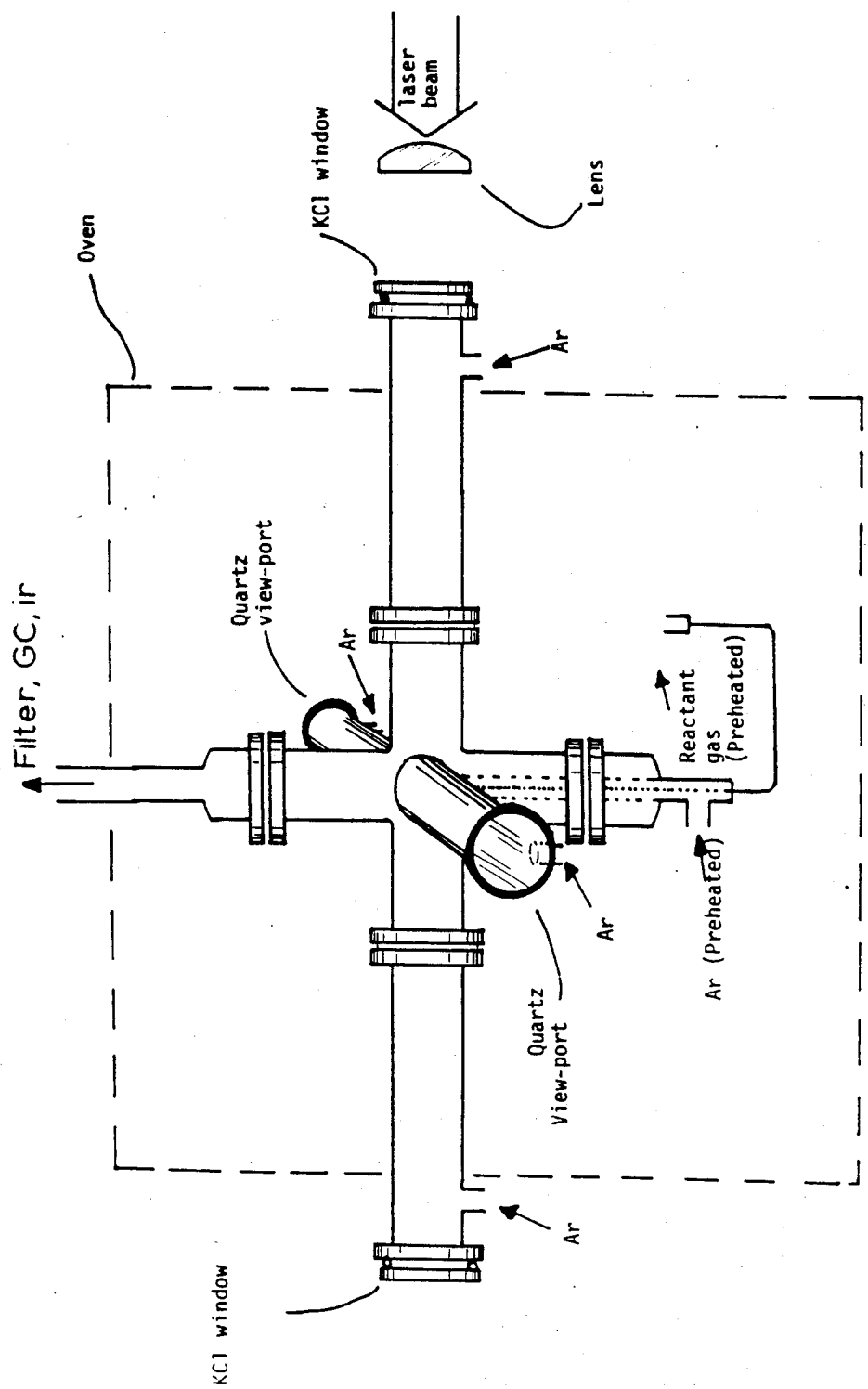
Figure 1. Laser Synthesis Reactor

IRON CARBIDE-BASED CATALYST PRODUCED IN THE PRESENCE OF LASER RADIATION

FIELD OF THE INVENTION

This invention relates to a finely divided iron carbide-based catalyst which is produced by a gas phase pyrolytic decomposition reaction driven by a laser. The catalysts may be used to produce various hydrocarbons, including olefins, from CO and $H_2$.

BACKGROUND OF THE INVENTION

The Fischer-Tropsch reaction involves the catalytic hydrogenation of carbon monoxide to produce a variety of products ranging in size and functionality from methane to higher alcohols. The methanation reaction was first described by Sabatier and Senderens in 1902. The later work of Fischer and Tropsch dealing with higher hydrocarbons was described in Brennstoff-Chem. 7, 97 (1926).

The reaction is highly exothermic and care must be taken to design reactors for adequate heat exchange capacity. Nevertheless, substantial research has been undertaken in the interim since the initial characterization of the reaction during the 1920's. The process is especially suitable for use when carbonaceous feedstocks of otherwise low economic value are available. For instance, the first major commercial use of the Fischer-Tropsch process was in Germany during the mid-30's. By the beginning of World War II, Germany was producing nearly 11,000 B/D of primary products using mainly the cobalt based catalyst described by Fischer and Pichler (Ger. Pat. No. 731,295—issued Aug. 2, 1936). The feedstock was, in general, based on available coals.

Subsequently, a consortium of nine American companies designed and built a plant at Brownsville, Texas based on an iron based catalyst. The plant was completed in 1950 and had a design capacity of 50MMSCFD. Various economic and technical difficulties caused final shutdown of the plant in the late 50's.

A rasonably economic use of the process has been practiced in South Africa in the SASOL plants. These plants use an iron-based catalyst and produce gasoline and waxes by gasifying a somewhat low-grade coal to produce a synthesis gas for feed to the Fischer-Tropsch reactors.

Research continues in this area because of the potential for converting low value feedstocks into higher value products.

The chemistry of the Fischer-Tropsch reactions is, in a gross sense, quite simple. The overall reactions for the production of alkanes (No. 1), alkenes (No. 2) and alcohols (No. 3) are as follows:

1. $\begin{cases} (2n+1)H_2 + nCO \longrightarrow C_nH_{2n+2} + nH_2O \\ (n+1)H_2 + 2nCO \longrightarrow C_nH_{2n+2} + nCO_2 \end{cases}$ 2. $\begin{cases} 2nH_2 + nCO \longrightarrow C_nH_{2n} + nH_2O \\ nH_2 + 2nCO \longrightarrow C_nH_{2n} + nCO_2 \end{cases}$ 3. $\begin{cases} 2nH_2 + nCO \longrightarrow C_nH_{2n+1}OH + (n-1)H_2O \\ (n+1)H_2 + (2n-1)CO \longrightarrow C_nH_{2n+1}OH + (n-1)CO_2 \end{cases}$ The types and amount of products obtained via such reactions are typically dependent upon the reaction conditions and choice of catalyst.

Few of the catalysts used in the past have been either very selective or very active. Those catalysts that were selective or active were uneconomic for other reasons, e.g., sensitivity to sulfur poisoning or used high cost catalytic metals such as ruthenium.

The catalyst of the present invention is iron/carbon-based. Because of the method of its preparation, the catalysts has high selectivity and/or conversion at reaction conditions considered to be quite moderate.

As noted above in the historical discussion, iron-bearing catalysts were among the first ever used in the Fischer-Tropsch reaction. Indeed, Fischer and Tropsch believed that carbides were an intermediate in the overall reaction. Later kinetics work suggested carbides could not be an intermediate in the process. Hall et al, J. Soc. Chem. Ind. London 65, 128 (1946); Weller, J. Am. Chem. Soc. 69, 2432 (1947) and; Kummer et al, J. Am. Chem. Soc. 70, 3632 (1948). However, the reduced metallic iron, as used in the Lurgi-Ruhrchemie fixed bed process, appears to change from the original $\alpha$-Fe phase to a mixture of $\alpha$-Fe, $Fe_3O_4$, FeC and $Fe_2C$ as conversion operations continue. See, Malan et al Brennstoff-Chem. 42, 209–212 (1961).

The present invention, as will be discussed below in greater detail, involves the use of a laser to pyrolize low valence iron-carbon bearing compounds to produce a fine particle iron-carbon containing catalyst. At least a portion of the catalyst is the iron carbide, cementite.

Others have described the use of iron-carbon containing catalysts produced by laser pyrolysis in Fischer-Tropsch reactions. The work of Gupta et al (in U.S. Pat. No. 4,468,474), issued Aug. 28, 1984 and in SPIE 458, Appl. of Lasers to Industrial Chemistry, 131–139 (1984)) shows the production of iron, carbon and silicon-containing catalysts by a laser and the catalysts' subsequent use in the Fischer-Tropsch process. Moderate activity and high $C_2$–$C_4$ olefin selectivity is asserted for the catalysts.

Applicants' catalysts contain substantially no silicon.

No known prior art is believed to show the production of the unique catalyst described below, the catalyst itself and the attributes of the catalyst in the production of hydrocarbons.

SUMMARY OF THE INVENTION

The invention has several closely interrelated parts. The first deals with a process for pyrolyzing a volatile iron-carbon-containing-compound, optionally in the presence of an additional carbon containing compound, with a laser to produce a unique Fischer-Tropsch catalyst comprising iron and carbon but substantially no silicon.

The fine particle iron-carbon Fischer-Tropsch catalyst resulting from the laser pyrolysis step is considered to be an integral part of the invention.

Other variations of the invention involve processes using those catalysts in a Fischer-Tropsch reaction to produce hydrocarbons from CO and $H_2$ generally and, specifically, to produce $C_2$–$C_4$ olefins.

BRIEF DESCRIPTION OF THE DRAWINGS

The drawing is a schematic representation of the laboratory device used to prepare the inventive catalyst used in the Examples.

DESCRIPTION OF THE PREFERRED EMBODIMENTS

The present invention provides a finely divided catalyst composition comprising iron and carbon, at least a portion of which is an iron carbide, which is active for the conversion of carbon monoxide and hydrogen into a product mixture of 80% or more $C_2$-$C_4$ alkenes.

The iron-carbon catalyst composition of the instant invention may be prepared by gas phase pyrolytic decomposition of a volatile organic iron-containing compound (optionally in the presence of an additional carbon source) in the presence of a laser emission under conditions of laser power absorption, reactant and/or diluent flow rate and pressure to produce finely divided iron-carbon containing catalyst particles.

The organic-iron-containing compounds generally are iron carbonyls. Compounds such as $Fe(CO)_5$, ferrocene, and iron acetylacetonate are all suitable; $Fe(CO)_5$ is especially preferred. The optional carbon source may act only as a diluent, depending upon reaction conditions, or may add a source of carbon to the pyrolysis reaction. The preferred carbon sources are short chain olefins such as ethylene. Obviously, at least one of the components must absorb the radiated laser energy.

The partial pressure of the organic-iron-containing compounds depends upon the total pressure of the reactor but may be in the range of 20 to 500 torr; the optional carbon source may be 20 to 500 torr and a diluent such as argon or other noble gas may be included to bring the overall system pressure to a total of 200 to 1000 torr.

By "finely divided" Fe-C catalyst particles is meant those having average diameters between 1 and 100 nm, preferably 10–50 nm. The materials usually have a BET surface area of 15 to 50 $m^2/gm$, preferably 20–35 $m^2/gm$. The iron-carbon catalyst is at least a major portion cementite, $Fe_3C$. The catalyst is a mixture of phases and, in addition to the cementite, includes $\alpha$ and $\gamma$ phase iron. The surface iron of the as-produced catalyst is carbidic iron. The $\alpha$ and $\gamma$-Fe phases appear to be embedded in the cementite. In some cases, the varying phases appear to be more than a simple physical mixture and may constitute a nonequilibrium mixture. A minimum amount of carbonaceous material is present on the exterior surface of the catalyst as a coating. The coating acts as a moderate passivating agent. No hydrogen pretreatment is needed to activate the as-prepared catalyst. The catalyst, as produced, is not pyrophoric. The catalyst contains less than about 1.0% oxygen and is substantially bereft of silicon. Although the method of producing this catalyst is believed to produce, of itself, a catalyst which is unique, the catalyst itself desirably contains no more than about 20% total carbon, preferably no more than about 12% total carbon and most desirably between 8% and 12% total carbon. It should be noted tht the higher the percentage of excess matrix carbon, the generally lower the amount of $C_{10}$ olefins produced.

The laser used is preferably a continuous wave (cw) type capable of producing a flux of about 200 to 10,000 $W/cm^2$ in the reaction zone and further capable of resonant adsorption by a substance in the reaction zone. A $CO_2$ laser of adequate size is desirable. The residence time of the reactants in the laser beam should be between 1 and 60 ms. The quench rate for the products leaving the zone should be such that the total time the reactant/products are at the elevated temperature is 0.15 seconds or less. Quenching may be provided mainly by radiative energy loss from the reaction products.

It is to be understood tht the reactor pressures and gas flow rates described herein are not critical to the synthesis of the catalyst, but are merely convenient for the particular reactor design employed. The only requirements are that the operating conditions be such that the time scale of the reaction be short enough to prevent deposition of excess carbon on the solid particles produced in the reaction, and that temperatures sufficient to drive the reaction be reached. Depending upon the power of the particular laser used to drive the reaction and the design of the particular reactor used to conduct the synthesis, a wide range of reactor pressures and gas flow rates will allow preparation of the catalyst.

By changing the reaction conditions, it is possible to obtain other products from the same reactants. For example, increasing the $Fe(CO)_5$:$C_2H_4$ ratio to 1:4 while maintaining the same laser power yields a product which is substantially all free iron and pyrophoric. Decreasing the residence time of the reactants in the laser beam has substantially the same effect. Similarly, increasing the laser power, or otherwise raising the reaction temperature, increases the carbon content of the product by continued decomposition of $C_2H_4$. An increase in reaction time would have a similar effect.

The iron-carbon catalyst particles may be used as-is; e.g., in an appropriate slurry reactor, or may be supported in one fashion or another as known in the art. The catalyst may be integrated with known supports to produce a larger catalyst matrix which may be handled with ease.

Promoters such as alkali metals, preferably potassium, or alkaline earth metals, such as magnesium, may be added using known methods. For instance, up to 10% potassium, preferably 2%, may be added to the as-produced Fe-C catalyst by impregnation with an aqueous solution of a potassium salt such as potassium carbonate. More difficulty soluble materials may be ground and mulled with the product Fe-C catalyst prior to a compaction step such as pilling, tabletting or extruding.

Of course, for certain applications the iron carbide catalytic material may be placed on a refractory support such as alumina, silica, mullite, diatomaceous earth, silica-alumina co-mixtures or other materials known to provide high surface area.

The process for conversion of $CO/H_2$ to the various hydrocarbon products using the catalyst discussed above may be a fixed bed or preferably a slurry process. In the slurry process, the catalyst is suspended in a liquid hydrocarbon and the $CO/H_2$ mixture forced through the catalyst slurry allowing good contact between the $CO/H_2$ and the catalyst to initiate and maintain the hydrocarbon synthesis process. The slurry process is described in detail in such articles as Catal. Rev.—Sci. Engr., 21, 1980, pg. 225 (Kolbel, Ralek).

Advantages of a slurry process over that of a fixed bed process include better control of the exothermic heat produced in the Fischer-Tropsch process during the reaction and better control over catalyst activity maintenance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products residence time in the reaction zone.

The slurry liquid used in the process is a liquid at the reaction temperature, should be chemically inert under the reaction conditions and should be a relatively good solvent for $CO/H_2$ and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include $C_{10}$–$C_{50}$ linear or branched paraffinic hydrocarbons; the aromatic hydrocarbons include $C_7$–$C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. Representative examples of specific liquid slurry solvents useful are dodecane, tetradecane, hexadecane, octadecane, cosane, tetracosane, octacosane, dotriacontane, hexatritacosane, tetracontane, tetratetracontane, toluene, o-, m-, and p-xylene, mesitylene, $C_1$–$C_{12}$ mono- and multi-alkyl substituted benzenes, dodecylbenzene, naphthalene, anthracene, biphenyl, diphenylether, dodecylamine, di-nonylamine, trioctylamine, and the like. Preferred liquid hydrocarbon slurry solvent is octacosane or hexadecane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases.

The operating conditions for this process are generally as found below.

|  | Fixed Bed | Slurry |
| --- | --- | --- |
| T° C. | 240–300 | 240–280 |
| (pref.) | 250–275 | 250–275 |
| Press. (psig) | 50–200 | 50–200 |
| (pref.) | 50–120 | 50–120 |
| $H_2/CO$ | 0.5–9:1 | 0.5–9:1 |
| (pref.) | 1.8–2.5:1 | 1.8–2.5:1 |
| SHSV | 100–10,000 | 100–10,000 |
| (volume fresh gas/volume catalyst/hr) |  |  |
| Stirrer speed (rpm) | — | 600–4000 |
| Recycle gases | $C_4^-/CH_4/CO_2$ | $C_4^-/CH_4/CO_2$ |
| Diluent gases | $N_2/Ar/CH_4$/light hydrocarbons/$CO_2$ | $N_2/Ar/CH_4$/light hydrocarbons/$CO_2$ |

A magnetically stabilized fluidized bed as is described in U.S. Pat. No. 4,115,927 is also suitable for this reaction.

Having thus described the invention, the following are examples which illustrate the various workings of it. They are not intended to limit the invention in any way.

EXAMPLE 1

The catalyst was prepared in a high surface area, low excess carbon form by a gas phase pyrolytic decomposition reaction driven by a cw $CO_2$ laser. The reactants were $Fe(CO)_5$ and $C_2H_4$. The $C_2H_4$ also served to absorb energy from the laser beam, allowing rapid heating of the reactants to reaction temperature. Post-reaction quenching is also very rapid, preventing extensive decomposition of the $C_2H_4$ on the catalyst particles and thus minimizing excess carbon content of the solid.

The reactor is shown in FIG. 1. It was constructed around a mini-flange 6-way cross. As shown in the FIGURE, the vertical axis of the apparatus was used for introduction of the reactants and take-off of products. One horizontal axis was used for passage of the laser beam, while the remaining horizontal axis was used for monitoring the reaction. Argon inlets were provided near each of the four windows to prevent deposition of particulates on the windows. The $C_2H_4/Fe(CO)_5$ mixture entered the cell through a tube which was concentric with a slightly larger tube to a point 1–4 mm below the laser beam. The outer tube was used to provide an argon stream surrounding the reactant stream, thereby promoting stable flow of the reactants into the laser beam.

The laser was operated in a cw mode on the 10 P(20) line at 944 $cm^{-1}$. Although not resonant with the 950 $cm^{-1}$ Q-branch of $C_2H_4$, this line is absorbed strongly enough by weaker $C_2H_4$ absorption bands to drive the pyrolytic reaction. The laser produced about 150 W in a beam focused to 6 mm diameter at the reaction zone, yielding a flux of 500 $W/cm^2$.

The synthesis was conducted at a reactor pressure of about 300 torr. The total argon flow to the four cell windows was about 70 SCCM (cc/min @ STP), while the argon flow coaxial to the reactants was also 70 SCCM. The $C_2H_4/Fe(CO)_5$ mixture was provided by bubbling $C_2H_4$ through liquid $Fe(CO)_5$ held at ambient temperature (23° C.) where the vapor pressure is 25 torr. [Gilbert, A. G.; Sulzmann, K. G. P., *J. Electrochem. Soc.* 1974, 121, 832–834.] The $C_2H_4$ flow rate was about 6 SCCM. Since the $Fe(CO)_5$ will essentially attain its equilibrium vapor pressure in the $C_2H_4$ stream under these flow conditions, the ratio of the reactants in the gas stream is determined by the total reactor pressure; $C_2H_4:Fe(CO)_5 = (300-25):25 = 11:1$.

The laser-driven reaction gave a bright yellow flame, indicating that quite high temperatures were obtained. Under the flow and pressure conditions given above, the residence time of the reactants in the laser beam is 25–40 ms and the quenching rate should be fast enough to keep the total time at high temperature, e.g., above about 500° C., to 0.1 s or less.

The solid products were collected on an 0.5 μm-pore Teflon membrane filter. The gaseous products were monitored by gas chromatograph (gc) and infrared detectors (ir). The ir showed that conversion of $Fe(CO)_5$ to products was quantitative under reaction conditions. The characteristic ν(CO) bands of $Fe(CO)_5$ could not be seen in the product gases, though free CO was present. The GC showed that most of the $C_2H_4$ did not react. The gas yields were to some extent dependent upon the linear flow rate of the reactant stream at the laser beam as shown below. Since the reactant stream does undergo some spreading as it enters the reactor, the linear velocity decreases with distance from the inlet tip. Raising the laser beam further above the inlet tip, or alternatively, decreasing the flow rate of the reactants, led to increased residence time of the reactants in the beam. The gas yields then indicated higher reaction temperature, or a longer reaction, or both, as demonstrated by the increase in yields of $C_2H_2$ and $CH_4$ relative to $C_2H_4$.

| | Measured Mole %, TCD | |
|---|---|---|
| Gas | High Flow | Low Flow |
| $C_2H_4$ | 64 | 57% |
| CO | 32 | 29% |
| $C_2H_2$ | 3.3 | 12.5% |
| $CO_2$ | 0.67 | 0.08% |
| $CH_4$ | 0.50 | 1.55% |

$H_2$ was also observed, but the peak area is not meaningful (He carrier). A peak for $C_2H_6$ could be observed by eye in the GC trace, but was so weak and broad that the integrator normally did not detect it. The yield was measured at 0.06% of the gases in one instance.

The analysis of one sample of solid prepared by the above method was: Fe, 86.2%; C, 12.74%; O, 1.73%; H, <0.35%. X-ray diffraction showed that the major phase present was $Fe_3C$ or cementite. The BET surface area was 27 $m^2/g$, and XPS showed that the surface was carbon rich, with only Fe and C present. The catalyst so prepared was not pyrophoric acid and did not appear to oxidize significantly in air. Analysis by Mössbauer spectroscopy showed that $Fe_3C$ was the major phase, with smaller amounts of $\alpha$-Fe and $\gamma$-Fe also present.

EXAMPLE II

Gas streams containing $Fe(CO)_5/C_2H_4$ were pyrolyzed using the method of Example I, with a cw $CO_2$ laser producing about 200 W, to yield powders containing Fe and C. The total pressure of the reactant gases was 385 torr. The partial pressure of $Fe(CO)_5$ and the flow rate of the $C_2H_4$ were varied. Analytical results for the powders are shown below.

| Synthesis | (a) | (b) | (c) | (d) |
|---|---|---|---|---|
| $Fe(CO)_5$ partial pressure, torr | 92 | 73 | 73 | 30 |
| $C_2H_4$ flow rate, ccm | 15 | 15 | 35 | 35 |
| Powder analysis, % Fe | 92.9 | 90.9 | 89.6 | 87.0 |
| Powder analysis, % C | 8.15 | 9.04 | 8.60 | 10.80 |
| Powder surface area, $m^2/g$ | 20.4 | 22.2 | 24.1 | 34.8 |

All powders were shown to be mainly $Fe_3C$ by X-ray diffraction.

These results demonstrate that the powder composition can be controlled by varying the preparation conditions.

EXAMPLE III

Catalyst (1)

Samples of $Fe_3O_4$ were reduced in flowing $H_2$ at 450° C. for 5-7 hours and then treated in $H_2/CO$ at 350° C. until the X-ray diffraction pattern indicated that all the iron was converted to a carbide phase, predominantly of the form $Fe_5C_2$ and $Fe_3C$ in a matrix of 40-70% wt. of an amorphous carbon phase. This catalyst was transferred directly to the reactor and brought up to reaction temperature and pressure under a $CO/H_2$ mixture.

Catalyst (2)

A gas stream containing $Fe(CO)_5/C_2H_4$ was pyrolyzed using the method of Example I with a CW $CO_2$ laser to yield a powder containing Fe and C as the only detectable components with ca. 5-15% wt. of an amorphous carbon phase.

The performance of these two catalysts under continuous stirred tank reactor conditions is shown below.

| Catalyst | (1) | (2) |
|---|---|---|
| v/v cat/hr | 2000 | 4000 |
| % CO conversion | 71.9 | 82.5 |
| Wt. % selectivity ($CO_2$ free basis) | | |
| $CH_4$ | 16.1 | 9.5 |
| $C_2°$ | 9.7 | 5.4 |
| $C_2=$ | 3.0 | 7.5 |
| $C_3°$ | 5.6 | 1.3 |
| $C_3=$ | 10.9 | 10.5 |
| $C_4°$ | 3.0 | 1.1 |
| $C_4=$ | 5.0 | 9.0 |
| % olefin in $C_2-C_4$ | 50.7 | 77.6 |

Conditions: 270° C., 2/1 $H_2/CO$, 200 SCCM, 75 psi, octacosane solvent, 600 rpm. The $H_2/CO$ mixture was run directly through the reactor without recycle of product gases.

The results demonstrate the high activity and olefin selectivity provided by the laser generated Fe-C catalyst (2) relative to the conventionally prepared iron carbide catalyst (1).

EXAMPLE IV

Catalyst 3

Samples of the laser generated Fe/C catalyst (2) of the invention were treated with $H_2/CO$ at 350° C. to generate an amorphous carbon phase equivalent to that present in the conventionally prepared iron carbide catalyst (1).

The performance of the $H_2/CO$ treated laser generated Fe/C catalyst relative to the conventional iron carbide catalyst (1) is shown below.

| Catalyst | (1) | (3) |
|---|---|---|
| v/v cat/hr | 2000 | 5000 |
| % CO conversion | 71.9 | 33.0 |
| Wt. % selectivity ($CO_2$ free basis) | | |
| $CH_4$ | 16.1 | 11.1 |
| $C_2°$ | 9.7 | 7.3 |
| $C_2=$ | 3.0 | 16.6 |
| $C_3°$ | 5.6 | 1.0 |
| $C_3=$ | 10.9 | 9.0 |
| $C_4°$ | 3.0 | 0.6 |
| $C_4=$ | 5.0 | 6.6 |
| % olefin in $C_2-C_4$ | 50.7 | 80.0 |
| % olefin in $C_{10}^+$ | N.A. | 35.0 |

Conditions: 270° C., 2/1 $H_2/CO$, 200 SCCM, 75 psi, octacosane solvent, 600 rpm.

These results show the improved olefin selectivity achieved with the laser generated Fe/C catalyst (3) that contains amorphous carbon at levels found in the conventional iron carbide synthesis catalyst (1). However, the presence of excess matrix carbon decreases (as shown by comparison with catalyst (2)) the amount of liquid $C_{10}^+$ olefin.

EXAMPLE V

Catalyst (4)

A laser synthesized Fe/Si/C composition analogous to that described by Gupta and Yardley was prepared by CW $CO_2$ laser pyrolysis of $Fe(CO)_5/C_2H_4/SiH_2(CH_3)_2$.

The behavior of this material relative to the Si-free catalyst (2) of the invention are shown below.

| Catalyst | (2) | (4) |
|---|---|---|
| v/v cat/hr | 4000 | 500 |
| % CO conversion | 82.5 | 5.0 |
| Wt. % selectivity (CO$_2$ free basis) | | |
| CH$_4$ | 9.5 | 15.9 |
| C$_2$° | 5.4 | 6.0 |
| C$_2$= | 7.5 | 3.0 |
| C$_3$° | 1.3 | 15.0 |
| C$_3$= | 10.5 | 12.0 |
| C$_4$° | 1.1 | 6.0 |
| C$_4$= | 9.0 | 4.0 |
| % olefin in C$_2$-C$_4$ | 72.6 | 41.0 |

Conditions: 270° C., 2/1 H$_2$/CO, 200 SCCM, 75 psi, octacosane solvent, 600 rpm.

These results demonstrate the superior activity and selectivity provided by the Fe/C catalyst (2) of this invention relative to the Fe/Si/C catalyst (4).

EXAMPLE VI

The conventionally prepared iron carbide catalyst (1), the laser generated Fe/C (2) and Fe/Si/C (4) catalysts were examined under CSTR conditions: 270° C., 2/1 H$_2$/CO, 200 SCCM, 75 psig, octacosane solvent, 600 ppm. The yield and composition of liquid products collected at 4° C. and 15 psig were determined after 48 hours and are shown below.

| Catalyst | 1 | 2 | 4 |
|---|---|---|---|
| Wt. % C$_{10}$ (CO$_2$ free basis) | nil | 1.9 | nil |
| Distribution (%) | | | |
| 1-olefin | nil | 47.2 | nil |
| n-paraffin | — | 10.4 | — |
| n-alcohol | — | 1.1 | — |
| others | — | 36.5 | — |

The laser generated Fe/C catalyst (2) of this invention in contrast to the iron carbide (1) or laser generated Fe/Si/C catalyst (4) generates a recoverable C$_{10}$ fraction containing high levels of 1-olefin.

EXAMPLE VII

The laser generated Fe/C catalyst (2) was examined at 100 psig at 270° C. and 240° C. under CSTR conditions with 2/1 H$_2$/CO. The results of those tests are shown below:

| Temp. (°C.) | 240 | 270 |
|---|---|---|
| v/v cat/hr | 4000 | 4000 |
| % CO conversion | 43.9 | 89.3 |
| Wt. % selectivity (CO$_2$ free basis) | | |
| CH$_4$ | 5.9 | 6.4 |
| C$_2$° | 0.01 | 2.0 |
| C$_2$= | 6.0 | 4.9 |
| C$_3$° | 4.2 | 3.3 |
| C$_3$= | 8.1 | 9.7 |
| C$_4$° | 0.8 | 0.8 |
| C$_4$= | 5.6 | 8.3 |
| % olefin in C$_2$-C$_4$ | 80 | 79 |

These results demonstrate the high activity and olefin selectivity provided by the catalyst of our invention over a reasonably wide range of operating temperatures.

EXAMPLE VIII

The laser generated Fe/C catalyst (2) of this invention was impregnated with $K_2CO_3$ to yield a material containing 2% wt. K. This material was examined at 270° C., 2/1 H$_2$/CO, 4000 V/V cat/hr, 75 psig, octacosane, 600 rpm. The results are shown below:

| % CO conversion | 66.5 |
|---|---|
| Wt. % selectivity (CO$_2$ free basis) | |
| CH$_4$ | 5.6 |
| C$_2$° | nil |
| C$_2$= | 3.7 |
| C$_3$° | 0.5 |
| C$_3$= | 4.3 |
| C$_4$° | 0.3 |
| C$_4$= | 3.5 |
| % olefin in C$_2$-C$_4$ | 93.5 |

The results demonstrate the high olefin selectivity provided by the alkali promoted catalyst of our invention.

We claim as our invention:

1. A composition of matter comprising finely divided non-pyrophoric iron-carbon catalytic particles comprising iron and carbon in the substantial absence of silicon, a substantial portion of which is cementite, produced in a reaction zone in the presence of laser radiation under such conditions of laser flux density, power adsorption, concentration of iron compound reactants selected from the group consisting of iron carbonyls, iron acetylacetonate, and ferrocene, and pressure sufficient to produce non-pyrophoric iron-carbon particles having average diameters between 1 and 100 nm.

2. The composition of claim 1 wherein at least a portion of the iron is in the $\alpha$ and $\gamma$ phase.

3. The composition of claim 1 wherein the particles contain at least some free carbon.

4. The composition of claim 3 wherein at least some of said free carbon is situated on the particles' surface.

5. The composition of claim 1 wherein said average diameters are between 10 and 50 nm.

6. The composition of claim 1 wherein said iron compound is $Fe(CO)_5$.

7. The composition of claim 1 wherein said particles are supported on a refractory support.

8. The composition of claim 6, wherein the particles are supported on a refractory support.

9. A method for producing finely divided non-pyrophoric iron-carbon catalytic particles comprising the steps of: introducing an iron compound from the group consisting of iron carbonyls, iron acetylacentonate and ferrocene into a reaction chamber into which a laser is focused at such conditions of total pressure, iron compound partial pressure, laser energy flux density and power absorption that said finely divided particles are produced.

10. The process of claim 9 wherein the iron compound is $Fe(CO)_5$.

11. The process of claim 9 wherein an additional carbon-bearing compound is introduced into said reaction chamber.

12. The process of claim 11 wherein the carbon-bearing compound is a low molecular weight alkene.

13. The process of claim 11 wherein the carbon-bearing compound is ethylene.

14. The process of claim 9 wherein the laser energy flux density in said reaction chamber is between 200 and 10,000 W/cm$^2$.

15. The process of claim 14 wherein the laser used to produce said laser energy flux density is a $CO_2$ laser operating in the continuous mode.

16. The process of claim 14 wherein the residence time of the reactants in the reaction zone is between 1 and 60 ms.

* * * * *